United States Patent [19]

Austad

[11] Patent Number: 4,984,585

[45] Date of Patent: Jan. 15, 1991

[54] TISSUE EXPANDER

[76] Inventor: Eric D. Austad, 309 Riverview Dr., Ann Arbor, Mich. 48104

[21] Appl. No.: 484,867

[22] Filed: Feb. 26, 1990

Related U.S. Application Data

[63] Continuation of Ser. No. 467,115, Feb. 17, 1983, abandoned.

[51] Int. Cl.⁵ ............................................. A61B 19/00
[52] U.S. Cl. ......................................... 128/899; 623/8
[58] Field of Search ................. 623/8, 7, 11; 128/899; 604/96, 93

[56] References Cited

U.S. PATENT DOCUMENTS

| | | | |
|---|---|---|---|
| 2,168,427 | 8/1939 | McConkey | 128/344 |
| 2,813,531 | 11/1957 | Lee | 604/103 |
| 3,218,103 | 11/1965 | Boyce | 128/DIG. 20 |
| 3,626,949 | 12/1971 | Shute | 128/344 |
| 3,826,249 | 7/1974 | Lee et al. | 128/DIG. 20 |
| 3,884,242 | 5/1975 | Bazell et al. | 604/103 |
| 3,902,198 | 9/1975 | Rathjen | 3/36 |
| 4,055,187 | 10/1977 | Patel et al. | 604/103 |
| 4,217,889 | 8/1980 | Radovan | 128/1 R |

FOREIGN PATENT DOCUMENTS

| | | | |
|---|---|---|---|
| 54197 | 12/1980 | European Pat. Off. | 3/36 |
| 2742394 | 3/1979 | Fed. Rep. of Germany | 3/36 |

*Primary Examiner*—Stephen C. Pellegrino
*Attorney, Agent, or Firm*—Harness, Dickey & Pierce

[57] ABSTRACT

A tissue expander for implantation in a patient to expand skin and mucosal tissue comprises a low profile construction facilitating implantation in the patient and which is effective to promote a more uniform expansion free of overfolds in the expansion envelope which have been present in prior art devices. The expander of the invention comprises an envelope which is expansible by stretching. In one embodiment the envelope is separably mounted on the base and the base can be cut by the surgeon to conform its general shape to the need of any given patient.

4 Claims, 2 Drawing Sheets

TISSUE EXPANDER

This is a continuation of application Ser. No. 467,115, filed Feb. 17, 1983, now abandoned.

BACKGROUND AND SUMMARY OF THE INVENTION

This invention relates generally to surgical devices and procedures, and more specifically to an improvement in surgically implanted devices for expanding skin, mucus membrane, and other body tissues.

Tissue expansion is now a recognized modality of treatment in reconstructive surgery. It is based upon the following principle: Skin or mucus membrane reacts to a slowly enlarging mass beneath it by increasing in surface area. This is naturally-occurring phenomenon, most frequently displayed by the increase of abdominal surface area during pregnancy. Progressive obesity also illustrates this phenomenon.

One device developed by C. Radovan, causes this expansion phenomenon by means of an inflatable bag surgically implanted beneath the skin. The bag is connected by a tube to a reservoir which is also implanted. The bag is then incrementally inflated by hypodermically injecting a fluid into the reservoir from time to time. Inflation of the implant results in an increase in the surface area of overlying tissue. At a second operation, this implant is removed, and the overlying redundant tissue is utilized for reconstructive purposes. In some situations it may be stretched into a new position as a flap. In other situations, such as breast reconstruction, the tissue expander may be implanted beneath the skin at the site of the previously removed breast and simply replaced by a standard breast implant when expansion has been completed.

U.S. Pat. No. 4,217,889 in the names of C. Radovan and R. Schulte illustrates this type of device. There are also U.S. Pat. Nos. 4,190,040 and 3,310,051 which relate to this general subject.

The tissue expansion technique has been shown by the applicant to result in an increase in the reproduction rate of overlying skin; thus stimulation of new tissue is actually produced, rather than a simple "borrowing" of tissue from one area to another. In addition, because this expanded tissue is derived from immediately adjacent tissue, color and texture matching is optimized. Hair-bearing characteristics are also preserved. Finally, tissue expansion has been shown to result in a marked increase in blood supply to the expanded area; thus the tissue is made more desirable for reconstructive surgical purposes.

A second type of tissue expander, developed by R. Lapin differs physically from the Radovan implant in one significant way: The reservoir, by which injections are made, is located in the dome of the implant. Thus, the Lapin implant is slightly more compact, and does not require a connector tube.

A third type of tissue expander has been developed by the applicant. This is a self-inflating implant which is osmotically powered. The implant inflates over time at a predictable rate, via an influx of extracellular water. A hypertonic implant interior causes this influx.

The devices and procedures of Radovan have certain disadvantages, some of which have been described previously in applicant's prior U.S. Pat. No. 4,157,085. In addition, two new disadvantages of the devices and procedures of Radovan and Lapin have been identified and are described as follows.

The inflatable bag used in both the Lapin and Radovan expanders is made of medical-grade silicone of varying thickness from 10 mil (10/1000 inch) to 25 mil (25/1000 inch). When deflated and placed beneath the skin or mucus membrane, neither bag is readily compressed. Folding the bag upon itself results in multiple wrinkles and acute creases of the membrane. These irregular and unpredictable folds and creases gradually unfurl as the bag is inflated. However, in the early stages of inflation, three major problems arise from the presence of these folds and creases: First, the implanted device is unsightly due to multiple irregularities of the skin or mucosal surface caused by the folded bag. Second, these folds and creases create potential stress points within the membrane, which are subject to tearing and perforation (fold fault). Third, these folds and creases of the membrane cause untoward focal pressure on overlying soft tissue, and they may result in erosion of this tissue. Such erosion is catastrophic in that it results in potential bacterial contamination of the entire implant site which, if it were to occur, would usually necessitate implant removal and abandonment of the procedure.

A further major disadvantage of both the Radovan and Lapin devices relates to their inability to be readily modified, at the time of surgery, to meet the requirements and dimensions of some wounds. The bases of both types of implants are either circular or rectangular, depending on the style of implant selected, while the reconstruction may be best served by an expander of less standard conformation, such as a triangle, rhomboid, or semi-annulus.

The present invention is directed to a new and improved tissue expander overcoming the disadvantages of the prior art, particularly as described above with reference to the Lapin and Radovan expanders. Accordingly, one important advantage of the present invention is that skin tissue and mucus membrane can be more safely and aesthetically expanded.

Another advantage of the invention is that the tissue expander can be more conveniently implanted by the surgeon and adapted to the particular needs of any given patient for surgical reconstructive procedures.

The present invention in its preferred form is embodied by a relatively rigid base on which is disposed a flat envelope which, when uninflated, projects a smooth surface of minimal cross sectional height toward the undersurface of overlying tissue when implanted. The material of the envelope is expansible by stretching such that in response to introduction of expansion fluid, the envelope expands by stretching to exert a more uniform expansion force to the overlying tissue so as to alleviate the problems of prior art devices referred to above.

Moreover, as will be subsequently explained in greater detail, the envelope may comprise a single thickness layer of material whose perimeter is secured to the perimeter of the base so that both envelope and base define the expansion space which is expanded by the introduction of fluid. In another embodiment, means are provided for separably mounting the envelope on the base and with the envelope itself defining the expansion space and taking the form of a double thickness of said material disposed on and flat against the base when in the uninflated condition. In the last mentioned embodiment, the base may be cut from base material into a desired shape for use by the surgeon at his discretion in establishing the best shape for the tissue expander. The envelope, by being removably mountable on the base, can be readily conformed to the shape of the base which has been cut by the surgeon. In this way the tissue expander of the present invention in one aspect can be readily conformed to different shapes most suitable for the needs of any given patient.

The foregoing features, advantages and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

DESCRIPTION OF THE PREFERRED EMBODIMENT

Figure 1:
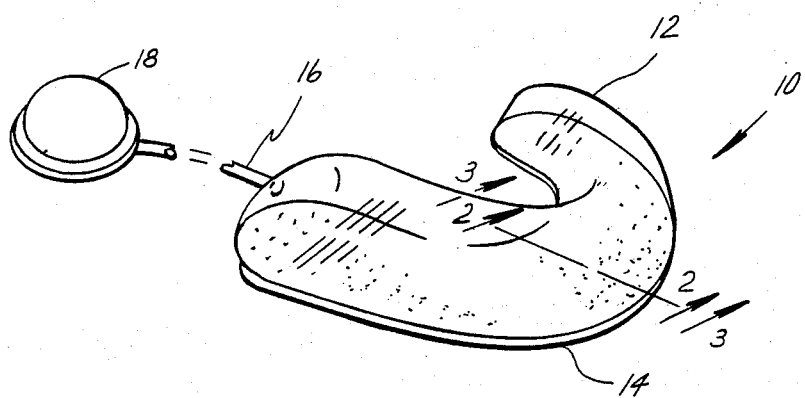
FIG. 1 is a perspective view illustrating a first embodiment of tissue expander of the present invention in an inflated, or expanded, condition by itself.
Figure 2:
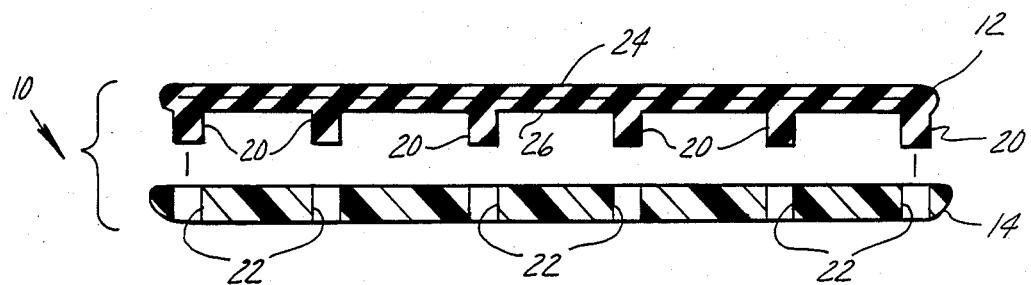
FIG. 2 is a transverse cross sectional view through the embodiment of FIG. 1 as taken in the direction of arrows 2—2 in FIG. 1 and enlarged and also illustrating the component parts in separated form, but in the deflated condition.
Figure 3:
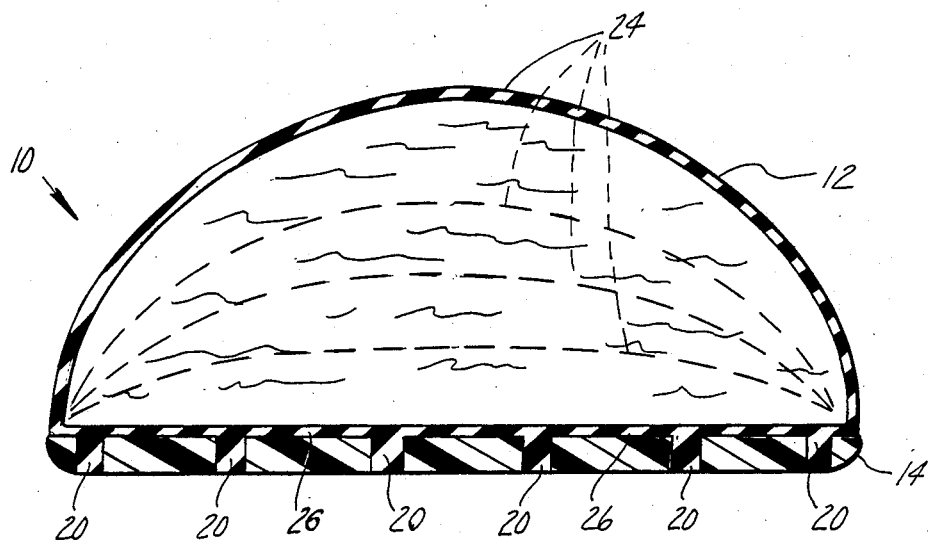
FIG. 3 is an enlarged transverse cross-sectional view taken through FIG. 1 in the direction of arrows 3—3.
Figure 4:
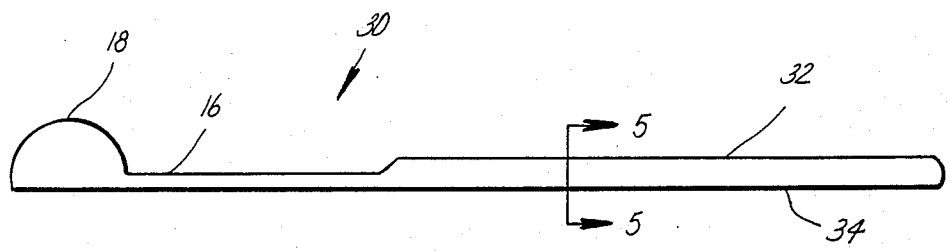
FIG. 4 is a side elevational view of another embodiment of tissue expander of the present invention in the initial deflated condition.

FIGS. 1, 2 and 3 illustrate a first embodiment of the low profile tissue expander of the present invention designated by the general reference numeral 10. This embodiment comprises an inflatable envelope 12 which is separably mounted on a more rigid base 14. As shown in FIG. 1 only, envelope 12 is connected by means of a connector tube system 16 to a reservoir 18 remote from the envelope. The remotely located reservoir 18 and connector tube system 16 represent pre-existent technology and provide a means for progressively introducing fluid into envelope 12 from a site remote from the implanted expander 10.

FIG. 2 illustrates the initial condition of the expander 10 at the time of implantation. Advantageously it is a low profile device having a minimum cross-sectional height. Although FIG. 2 illustrates envelope 12 in separated relation from base 14, the expander 10, in the assembled condition, has the envelope disposed substantially flat against base 14.

The envelope is rendered separably mounted on base 14 by means of a plurality of projections 20 integrally formed with envelope 12 and a plurality of apertures 22 in base 14. The illustrated form of envelope comprises a double thickness walled enclosure overlying base 14 with the double thickness wall being identified by upper and lower wall portions 24 and 26. Although separate reference numerals are given to these wall portions, it will be understood that the walled envelope is a complete enclosure except at the point of connection of the connector tube section 16. Hence, as will be seen, the envelope defines the expansible volume of the expander although its shape is determined at least in part by its mounting on base 14.

The projections 20 are provided on the exterior surface of the wall portion 26 and are arranged in a predetermined pattern. Preferably the shapes of all individual projections are identical, for example, each being a circular cylindrical projection. The apertures 22 are preferably arranged in a uniform pattern matching that of the projections 20. As such, the invention in this respect allows the envelope 12 to be separably mounted on base 14 by lodging projections 20 in apertures 22 such that the wall portion 26 is disposed essentially flat against base 14.

According to another aspect of the invention the envelope consists of a material which increases in volume by principally stretching. Thus, a major increase in the surface area of the envelope occurs. Hence, it is entirely unlike that described above in the Radovan device. The present invention as illustrated by the first embodiment 10 in the initial uninflated condition of the expander therefore comprises the two wall thicknesses 24 and 26 disposed against each other in substantially flat conditions. In other words the upper wall portion 24 as viewed in the drawing figure is essentially flat and substantially free of any overfolds as in the Radovan device. As such it is free from the wrinkles, creases and attendant disadvantages of the Radovan implant.

In assembled relation of envelope 12 and base 14, the wall portion 26 is disposed on and against base 14 during all stages of the expansion procedure. Envelope 12, unlike the Radovan envelope, consists of a material which allows for expansion of the volume of the envelope strictly by stretching of the envelope material. As such it is the wall portion 24 which progressively stretches as the expanded volume increases during the expansion procedure. Thus as can be seen in FIG. 3, the base 14 provides at least a substantially rigid support for the wall portion 26 so that conformance of the envelope to the general shape of the implant site is determined for the most part by the shape of base 14. The wall portion 24 expands to form an easily distended dome as seen in FIG. 3. The broken lines in FIG. 3 illustrate progressive stages of expansion between the initial essentially flat condition and the more fully extended condition illustrated by solid lines. It will be noted that the wall portion 24 stretches to apply expansion force over substantially the entire undersurface of the overlying tissue during all stages of the expansion procedure, remaining free from irregularaties, tissue erosion and like problems which do occur with prior types of devices. As such, the present invention offers a meaningful improvement in the physiological expansion process which benefits both the patient and surgeon. It can provide the surgeon a better condition of the skin for subsequent use in a surgical procedure as a flap or other reconstruction, and the patient is benefitted in terms of healing and appearance.

In use expansion takes place over a course of time by introducing appropriate amounts of expansion fluid into reservoir 18. At the conclusion of the expansion procedure the implant is removed according to conventional procedures, and the expanded skin or mucosal tissue is utilized for the intended reconstructive purpose.

The embodiment 10 illustrated in FIG. 1, 2 and 3 has a still further inventive aspect. It will be noted that the general overall shape of base 14 illustrated in FIG. 1 is a curvilinear one. The illustration in FIG. 1 is of a semi-annular or U-shape. Prior tissue expansion devices come in given shapes and sizes and hence in a given surgical procedure the surgeon must select from one of the existing available shapes and sizes. As a consequence it may happen that the surgeon must make special adaptations to his procedure to adapt it to the available shapes and sizes of the expanders.

In order to provide the surgeon with a greater ability to adapt a tissue expander to the needs of any given patient, the present invention provides for an arrangement wherein the base 14 may be cut to the desired shape by the surgeon, for example into the illustrated U-shape. After he has cut the shape of the base, the surgeon then mounts the envelope onto it in the manner explained above. The base 14 may be cut to a desired shape from base stock material which is provided with the pattern of apertures 22. The envelope 12 may come in a range of different sizes and shapes to accommodate different possible general shapes of bases, yet, the provision of the projections 20 on one of the wall surfaces, allows for the surgeon to conform this highly-elastic envelope to the general shape of the base which he has cut and to mount it on the cut base. If any given shape of envelope does not exactly conform to the requirements of the base, it is possible to cut off the unused or unnecessary projections 20 as the surgeon deems appropriate. Thus, it is possible to conform the envelope to the general overall shape of the base and because of the expansible strechable nature of the material of the envelope, the initial assembled condition of the implant can still comprise an essentially low profile construction substantially free of overfolds on the expanding surface.

The envelope and the base can be formed from any useful material which is biocompatible. Typical of such materials are cellulose acetate, crosslinked polyvinyl alcohol, polyurethanes, polyvinyl acetate, plasticized polyvinyl chloride and polyvinyl chloride, natural rubber, polybutadine and silicone rubber. Silicone rubber is the preferred material for both base and envelope not only because of its established biocompatibility but also because of its relative strength for the base and its strength and stretchability for the envelope. Modifications in the production of these polymers are capable of producing the desired physical qualities of both the envelope and the base.

Figure 5:
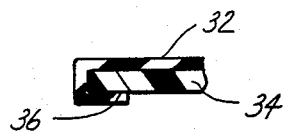
FIG. 5 is a fragmentary cross sectional view taken in the direction of arrows 5—5 in FIG. 4.
Figure 6:
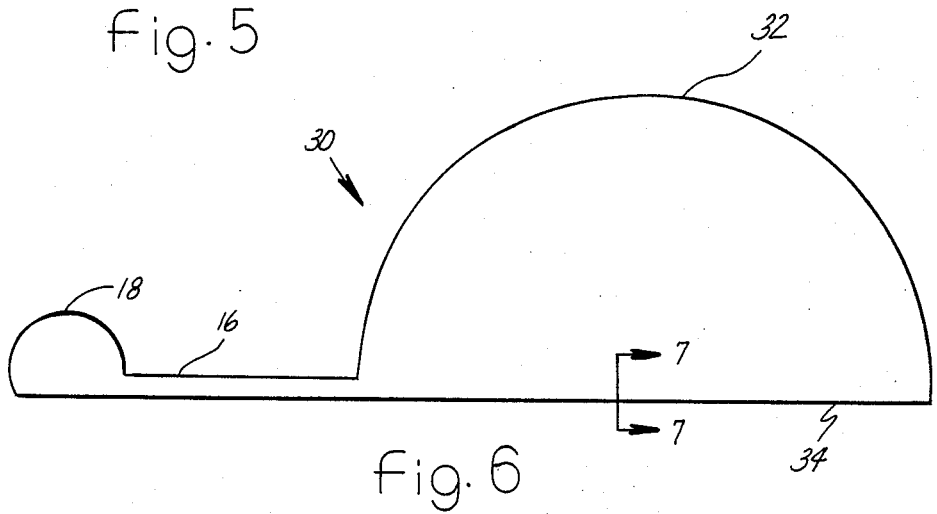
FIG. 6 is a view of the embodiment of FIG. 4 but in an expanded condition.
Figure 7:
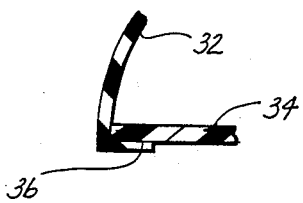
FIG. 7 is a fragmentary sectional view taken in the direction of arrows 7—7 in FIG. 6.

FIGS. 4 through 7 illustrate a second embodiment 30 of the present invention. In this embodiment, the envelope 32 and the base 34 cooperatively define the expansion space. The envelope 32 is a single thickness of material disposed flat on base 34. As can be seen in FIGS. 5 and 7, the base and envelope have perimeters which are secured together. In the illustrated construction the outer perimeter of envelope 32 is extended over, around, and beneath the outer perimeter of the margin of base 34 and the two are secured together at the adjoining portions indicated generally by the reference number 36. This embodiment lacks the separable mounting of the expander envelope on the base through the use of projections and apertures as in the first embodiment. It is however generic with the first embodiment in that both comprise the low profile construction free of overfolds in the expansion wall which exerts the expansion force on tissue during the expansion procedure.

Figure 8:
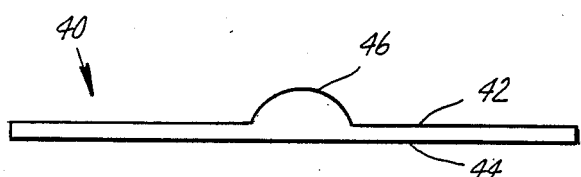
FIG. 8 is a side elevational view of still another embodiment of the invention shown in an initial unexpanded condition.
Figure 9:
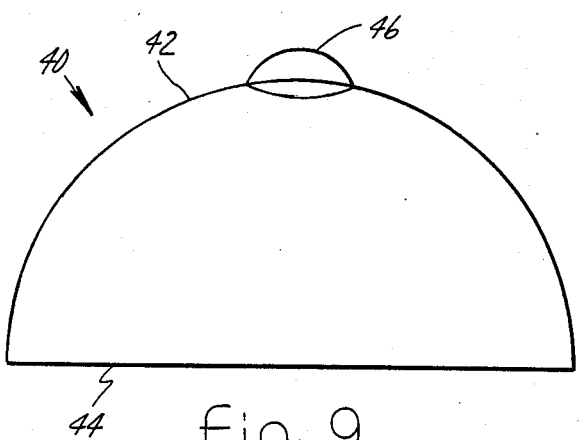
FIG. 9 is a view of the embodiment of tissue expander of FIG. 8 illustrating the expanded condition.

FIGS. 8 and 9 illustrate a third embodiment 40 which is the same as embodiment 30 insofar as it is a single wall envelope 42 whose outer perimeter margin is secured to the outer perimeter margin of its base 44. The reservoir 46 is formed with the dome in accordance with pre-existent technology so that the reservoir is not remotely located from the expansion space by means of a connector tube system as in the first two embodiments.

Each of the three disclosed embodiments possesses certain advantages for certain applications. Common to all embodiments is the low profile nature. The respective embodiments possess further unique individual features, such as separable mounting of the envelope on the base in embodiment 10 and the ability of that embodiment to be conformed in shape through the cutting of the base to a desired shape by the surgeon. Other procedures, such as molding, may be used to conform the base to a desired shape.

While a preferred embodiment of the invention has been disclosed it will be appreciated that principles of the invention may be applied to other embodiments.

What is claimed is:

1. A low profile expandable device for implantation beneath the skin and subcutaneous layers which, in situ, is progressively expanded in volume by the introduction of fluid, said low profile expandable device comprising a relatively rigid and generally planar base and an expansible envelope on said base, said expansible envelope defining the expansion volume, said expansible envelope being disposed essentially flat against the base and substantially free of overfolds when in its initial unexpanded condition so as to facilitate its implant in a patient, said envelope consisting of a material which is expansible by stretching such that as fluid is progressively introduced into the device, the envelope stretches to apply expansion force over substantially the entire undersurface of overlying skin and subcutaneous layers during all stages of the expansion procedure, said envelope comprising a double thickness of said material overlying said base, and means securing one of said double thicknesses to said base, said means securing one of said double thicknesses to said base comprising projections on said one thickness and apertures in said base with said projections being lodged within said apertures.

2. A low profile expandable device for implantation beneath the skin and subcutaneous layers which, in situ, is progressively expanded in volume by the introduction of fluid, said low profile expandable device comprising a relatively rigid and generally planar base and an expansible envelope on said rigid and generally planar base and an expansible envelope on said base, said expansible envelope at least in part defining the expansion volume, said expansible envelope being without nominal size and disposed completely flat against the base and substantially free of overfolds when in its initial unexpanded condition so as to facilitate its implant in a patient, said envelope consisting of a material which is expansible by stretching such that as fluid is progressively introduced into the device, the envelope stretches to apply expansion force over substantially the entire undersurface of overlying skin and subcutaneous layers during all stages of the expansion procedure.

3. A low profile expandable device for implantation beneath the skin and subcutaneous layers as set forth in claim 2 wherein said expansible envelope is a single thickness of said material having a perimeter portion corresponding to a perimeter portion of said base, said two perimeter portions being sealed together such that said base and said envelope cooperatively define the expansion volume.

4. A low profile expandable device for implantation beneath the skin and subcutaneous layers as set forth in claim 2 in which said expansible envelope defines said expansion volume, said envelope comprising a double thickness of said material overlying said base, and means securing one of said double thicknesses to said base.

* * * * *

UNITED STATES PATENT AND TRADEMARK OFFICE
CERTIFICATE OF CORRECTION

PATENT NO. : 4,984,585

DATED : January 15, 1991

INVENTOR(S) : Eric D. Austad

It is certified that error appears in the above-identified patent and that said Letters Patent is hereby corrected as shown below:

Column 6, Claim 2, lines 53-54, after "said", kindly delete "rigid and generally planar base and an expansible envelope on said".

Signed and Sealed this

Nineteenth Day of May, 1992

Attest:

DOUGLAS B. COMER

*Attesting Officer*     *Acting Commissioner of Patents and Trademarks*